United States Patent [19]

Mathis et al.

[11] Patent Number: 4,781,559
[45] Date of Patent: Nov. 1, 1988

[54] PLASTIC PELLET SORTING APPARATUS WITH EXTRUDED SIDE-STREAM MONITORING

[75] Inventors: Ronald D. Mathis; Gregory M. Swisher, both of Bartlesville, Okla.; Alejandro V. Santin, Houston, Tex.

[73] Assignee: Phillips Petroleum Company, Bartlesville, Okla.

[21] Appl. No.: 138,252

[22] Filed: Dec. 24, 1987

Related U.S. Application Data

[62] Division of Ser. No. 848,181, Apr. 4, 1986, Pat. No. 4,756,855.

[51] Int. Cl.⁴ .......................... B29B 7/72; B29C 47/92
[52] U.S. Cl. ..................... 425/135; 425/145; 425/174
[58] Field of Search ............ 264/40.1, 40.2, 40.7, 264/22; 425/135, 145

[56] References Cited

U.S. PATENT DOCUMENTS

| | | | |
|---|---|---|---|
| 4,442,054 | 4/1984 | Dane et al. | 264/40.1 |
| 4,448,736 | 5/1984 | Emery et al. | 425/145 |
| 4,721,448 | 1/1988 | Irish et al. | 264/40.2 |

Primary Examiner—Willard Hoag
Attorney, Agent, or Firm—George E. Bogatie

[57] ABSTRACT

An automated system is provided for selectively separating resin pellets having a gel count below a specified maximum from pellets having a gel count above the specified maximum, while the pellets are flowing in a pneumatic conveyor. The separation is based on an essentially continuous measurement in which a laser beam is utilized to detect the number of gels in a film made from pellets withdrawn as a sample stream from the main pellet stream. In response to the gel count measurement, a control signal is established that is utilized to manipulate a diverter valve located in the pneumatic conveyor, which diverts pastic pellet flow between a preferred storage means storing pellets having a low gel count and a secondary storage means for storing pellets having a higher gel count. In operation, a hold up tank is provided between the point from which the sample stream is withdrawn and the diverter valve, so that the plastic pellet flow can be delayed in the hold up tank for the amount of time required for the withdrawn sample stream to be converted into the film, whereby the gel count measurement is representative of the pellets passing through the diverter valve.

6 Claims, 1 Drawing Sheet

PLASTIC PELLET SORTING APPARATUS WITH EXTRUDED SIDE-STREAM MONITORING

This application is a division of application Ser. No. 848,181, filed Apr. 4, 1986 now Pat. No. 4,756,855.

This invention relates to resin pellets for use in manufacturing articles from thin plastic material such as films, sheets, blow molded articles, etc. which require large surface areas that are essentially free of flaws. In one aspect, this invention relates to a method for selectively rejecting, at an early time in a process, resin pellets which are unacceptable for the production of high quality plastic articles.

BACKGROUND OF THE INVENTION

Plastic resin is generally a high molecular weight polymeric material with no definite boiling point, but which is capable of flowing under heat and pressure, if necessary, into a desired final shape. Plastic articles are commonly produced from pellets formed of material comprising various blends of plastic resins and additives, wherein the resin pellets are extruded or molded to make the plastic article. In the production of plastic articles such as films, containers, etc., an important property of the article is the number and size of flaws that occur over a unit area of the article. One type of flaw that commonly occurs in plastic material is that of gels or fish eyes. As used herein gels and fish eyes are synonymous terms referring to a particle in a plastic material which differs from the surrounding resin to such a degree that it is not dispersed in the surrounding resin. Gels are readily discernable in thin plastic material.

In present processes for production of plastic pellets which typically contain gels, there is virtually no on-line method to detect flaws such as gels in the pellets as the pellets are being produced. Existing methods typically involve obtaining a sample of the pellets from a finished pellet transporting system as they are being produced, and performing a quality control test in a laboratory to determine if the pellets meet preestablished specifications. If the quality control sample fails to meet the specification standard, large quantities of produce made while the control sample was being analyzed may have to be downgraded or reprocessed. This obviously is expensive.

It is therefore an object of this invention to provide a method and apparatus for detecting, on line, flaws such as gels in the pellets so as to enhance quality control of the pellets by reducing the mixing of pellets having a low gel count from those having a high gel count.

SUMMARY OF THE INVENTION

According to this invention, method and apparatus are provided for selectively separating resin pellets having a gel count below a specified maximum, from pellets having a gel count above the specified maximum. The separation is based upon an essentially continuous measurement of the number of gels in a film produced from a sample stream of pellets withdrawn from the production line. The separation of the pellets in accordance with the present invention substantially reduces the mixing of pellets having significantly different gel counts.

In the preferred embodiment a control sample of plastic pellets is withdrawn as a side stream from a primary pellet stream at the end of a pellet production line, and the withdrawn side stream is passed to a small capacity extruder which produces a plastic film from the withdrawn sample stream. The plastic film is then passed along a predefined path of travel to an analyzing station where laser light analysis takes place. Means are provided in the analyzing station for scanning the laser light over the film being analyzed as it is moved through the analyzer. The analyzer records in a memory section each gel in the film which is of greater size than a predefined maximum, and accumulates a total for the number of gels recorded over a unit area of the film.

In a presently preferred embodiment a measurement signal is generated in the analyzer which is representative to the total number of gels in a unit area of film e.g. 75 gels per 30 sq. inches of film, where each gel is 5 mils or larger. In response to the measurement signal a control signal is automatically generated. The control signal has a first magnitude if the total number of gels in the analyzed section of film is above a predefined number, and has a second magnitude if the total number of gels is below the predefined number. The control signal is operatively connected to manipulating means for diverting the pellets so that pellets are sorted in a manner so as to separate pellets having a gel count below the specified maximum from pellets having a gel count above the specified maximum.

Further the present invention contemplates embodiments wherein the analysis signal supplied from the analyzer is representative of flaw parameters more detailed than the number of gels per unit area of the film that are larger than a specified size. For example the analyzer can detect other types of flaws such as black specks, holes, or scratches. In addition the analyzer can provide an output signal which is actually a plurality of signals representative of a plurality of flaw parameters, for example the number of gels between 3 mils and 5 mils in size, and the number of gels between 5 and 10 mils in size etc., the density of flaws in a unit area, and the type of flaws. From the plurality of signals provided by the analyzer, the control signal responsive to the analyzer signal can divert the flow in response to various combinations, or averages of the plurality of signals supplied by the analyzer.

Although the invention is applicable to the analysis of pellets produced from any polymeric material, it is of particular use with resinous thermoplastic polymer and most particularly of interest with polymers and copolymers of olefins such as ethylene, propylene, butylene, butadiene, styrene and the like.

Other objects and advantages of the invention will be apparent from the foregoing brief description of the invention and the claims as well as the detailed description and the drawings in which:

DESCRIPTION OF THE PREFERRED EMBODIMENT

Figure 1:
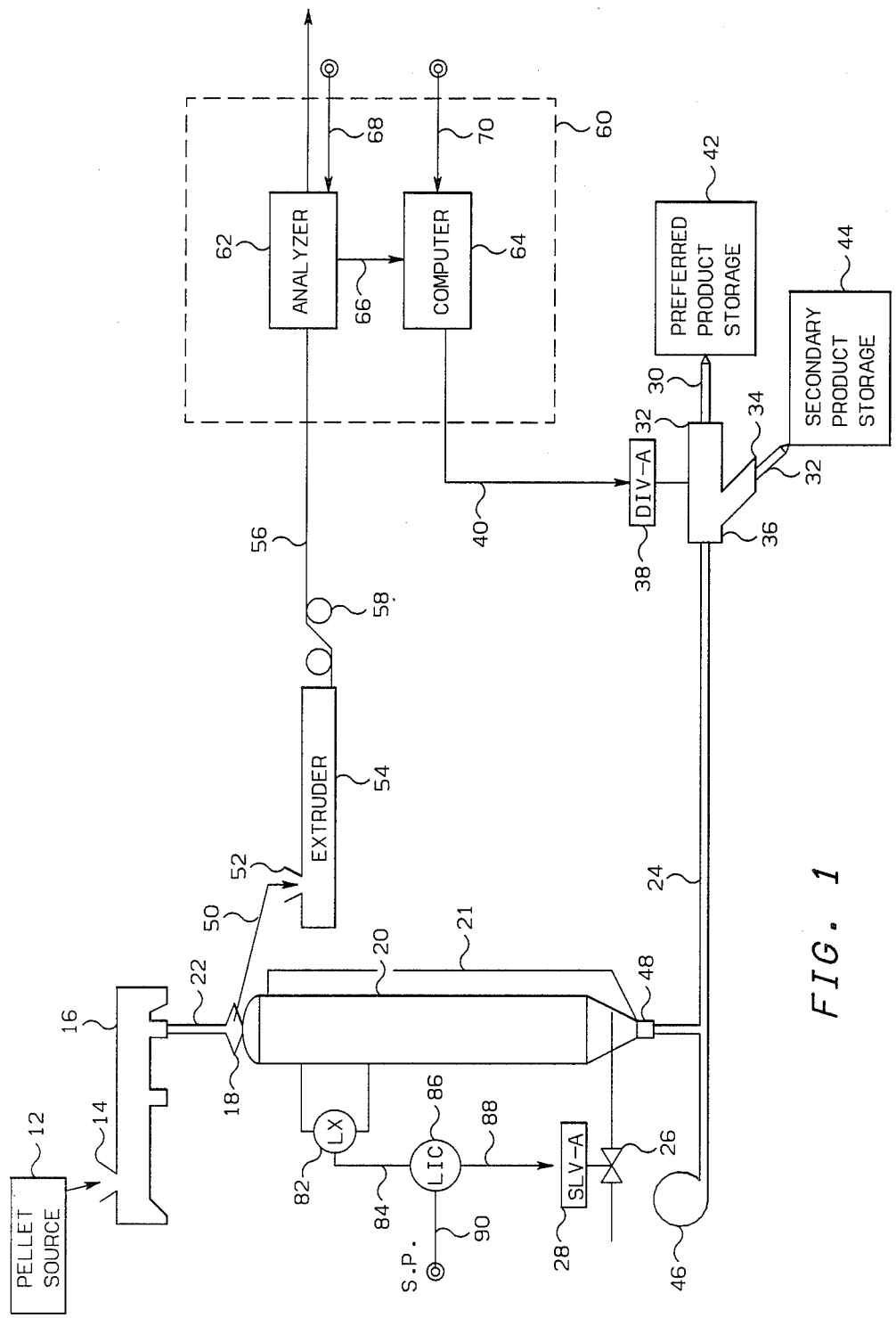
FIG. 1 is a diagrammatic illustration of a pellet sorting system having the flaw detection and control system of the present invention incorporated therein.

The invention is illustrated in terms of a simplified configuration of a pellet transport, analysis and control system. The primary flow of pellets is from a source of pellets through a classifying screen, then to the inlet of a hold up tank, and from the outlet of the hold up tank through a diverting valve to one of two collection tanks. A sample side stream of pellets as withdrawn through the inlet of the hold up tank and passed to an on-line extruder where the sample pellets are formed into a thin film. The film is passed to an analyzing station where it is subject to laser light analysis for determining flaws in the film. In response to the laser analysis a control signal is developed which manipulates the diverter valve and thus sorts the pellets in response to the analysis so that pellets are separated from on the basis of the number of flaws contained in the pellets.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. Transducing of these signals from electric to pneumatic form or from pneumatic to electric form is not illustrated for the sake of simplicity because it is well known in the art that if a parameter is measured in pneumatic form it must be transduced to electrical form if it is to be transmitted in electrical form by a transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signal based on measured analysis parameters as well as set points supplied to the computer. Analog computers or other types of computing devices could also be used in the invention.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such a proportional, proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilized a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw measurement signal produced by a differential pressure meter could exhibit a generally proportional relationship to the square of the actual parameter. Other measuring instruments might produce a signal which is directly proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved reardless of the exact mathematical relationship between the signal units and the measured or desired process units.

Referring now to FIG. 1, there is shown a control system for sorting pellets based on an actual analysis of flaws appearing in a unit area of film produced from a representative sample stream of the pellets.

The pellets to be sorted are provided from a source of pellets 12 which preferably is a conveyor feeder but can be any known type of feeder which can feed pellets at an essentially constant rate to the feed port 14 of classifying screen 16. An important function of classifying screen 16, which is a shaker screen, is to minimize the number of agglomerated pellets that pass with the individual pellets to the feed port 18 of hold up tank 20 through pellet conduit means 22.

Hold up tank 20 is preferably a tubular vessel mounted vertically with the inlet feed port 18 at the upper end. Hold up tank 20 is also provided with a pressure equalizing conduit 21 extending from outlet 48 of the hold up tank 20 to a point above the level of pellets in tank 20. In tubular tank 20 plug type flow is established where each element of material essentially remains in the hold up tank for the same amount of time. As will become apparent hereinafter, the hold up delay in tank 20 is desirable to compensate for the dead time involved in analyzing the film 56 in the analyzer section 62 of the automatic inspection and control unit 60.

It is recognized that separation of pellets in a system as shown in FIG. 1, but without the hold up tank 20 is possible. However, operation of system without the hold up tank 20 results in a greater degree of mixing of pellets which have significantly different gel counts and is therefore less efficient than a system which includes the hold up tank 20.

From the hold up tank 20, pellets are transferred through a control valve 26 located at the outlet 48 of hold up tank 20. Control valve 26 which is preferably a slide valve, is positioned by actuator 28 to control the transfer of plastic pellets from hold up tank 20 to pneumatic transfer line 24. Blower 46 is provided for the pneumatic transfer line 24. The pellets in pneumatic transfer line 24 are delivered to either a preferred grade product storage container 42 via outlet 32 of diverter valve 36 and conduit means 30, or to a secondary grade product storage container 44 via outlet 34 of diverter valve 36 and conduit means 32, in accordance with the control signal 40 applied to actuator 38 of diverter valve 36, as will be explained more fully hereinafter.

Conduit means 50 communicating between feed port 18 of hold up tank 20 and feed port 52 of exterior 54, delivers a sample stream of pellets to extruder 54. Extruder 54 produces a sample film 56 from the sample stream of pellets flowing in conduit means 50 which has the characteristics of film produced from the primary pellet stream flowing in conduit means 22. The film 56 is passed through rollers 58 and is then passed through a continuous laser automatic inspection and control unit 60 where 100 percent inspection of the film is provided as it moves through the unit 60.

For convenience, unit 60 is considered to be divided into an analyzer section 62 and a digital computer 64. In analyzer section 62 the film is subjected to laser light radiation and using defraction techniques along with electronic discriminator techniques, an internal signal is generated responsive to the size of each gel. The analyzer section 62 is also provided with signal 68 which is representative of the minimum gel size to be reported by analyzer 62. In response to signal 68 and the internally generated signals, analyzer 62 provides an essentially continuous measurement signal 66 which is representative of the number of gels in a unit area film 56 that are greater than the gel size represented by signal 68.

Signal 66 is provided from the analyzer section 62 to the computer 64 of unit 60. Computer 64 is also provided with a signal 70 which is representative of the number of gels in a unit area film that are acceptable for delivery of the primary pellet stream flowing in conduit means 24 to the preferred product storage container 42. In response to signal 66 and 70 computer 64 provides a control signal 40 which has a first magnitude if signal 66 is greater than signal 70 and has a second magnitude if signal 66 is less than signal 70. Control signal 40 as previously stated is provided to the actuator 38 of diverter valve 36, and diverter valve 36 is manipulated in response thereto.

The laser automatic inspection and control unit 60 which includes analyzer section 62 and digital computer 64 and means for providing an output signal 40 is preferably a laser automatic inspection unit known as the INTEC 5000, which is commercially available from INTEC, Trumbull, Conn. 06611. The values for signal 68 and 70 which are representative respectively of the minimum gel size to be reported by analyzer section 62 and the number of gels appearing in a unit area film that are acceptable for preferred product storage are generally well known and can be entered by an operator.

Level transducer 82 in combination with level sensing instrumentation located in hold up tank 20 provides an output signal 84 representative of the level of plastic pellets in hold up tank 20. Signal 84 is provided as a process variable input to level controller 86. Level controller 86 is also provided with a set point signal 90 which is representative of the desired level of pellets in hold up tank 20. The level controller 86 provides an output signal 88 which is responsive to the difference between signals 84 and 90. Signal 88 is provided as a control signal to actuator 28 of control valve 26 which is operably located in outlet 48 of hold up tank 20.

The value for signal 90 which is representative of the desired level of plastic pellets in hold up tank 20 will depend on the feed rate of plastic pellets to hold up tank 20 and the dead time between sampling pellets flowing in conduit means 22 and generating a control signal 40 from computer 64 corresponding to the sample. In operation, both the feed rate and dead time will be assumed constant and signal 90 can be estimated and entered by an operator. As an example calculation of set point signal 90, assume a production rate of 10,000 pounds per hour and an analysis dead time of 1.5 minutes. The production in 1.5 minutes is (10,000 lbs/hr) (1 hr/60 min) (1.5 min)=250 lbs Assuming a bulk density for the plastic pellets of 38.6 pounds per cubic foot, the required volume for the hold up tank is (250 lbs)×ft$^3$/38.6 lbs=6.47 ft$^3$ If the hold up tank is twelve inches in diameter, the level required would be 8.23 feet.

The invention has been described in terms of a presently preferred embodiment as illustrated in FIG. 1. Specific components used in the practice of the invention such as level transducer 82, level controller 86, control valve 26 and 28, valve actuators 28 and 38 are each well-known available control components such as are described for example in *Perry's Chemical Engineering Handbook*, 5th Addition, Chapter 22.

While the invention has been described in terms of the presently preferred embodiment, reasonable variations and modifications are possible by those skilled in the art of material handling, and such modifications are within the scope of the described invention and the appended claims.

That which is claimed is:

1. Apparatus comprising:
    (a) a hold up tank having an inlet and an outlet;
    (b) means for supplying a main stream of plastic pellets through a classifying screen to said inlet of said holdup tank wherein said classifying screen minimizes the number of agglomerated pellets that pass with the individual pellets to said holdup tank;
    (c) a diverter valve having an inlet and first and second outlets;
    (d) means for supplying said main stream of plastic pellets from said outlet of said holdup tank to said inlet of said diverter valve;
    (e) an extruder for converting plastic pellets to plastic film;
    (f) means for withdrawing a side stream of plastic pellets from said main stream at a sampling point at said inlet of said holdup tank and for providing said side stream to said extruder;

(g) analyzer means for analyzing for at least one type of flaw in a moving plastic film;

(h) means for passing a plastic film from said extruder to said analyzer means, wherein said analyzer means generates a measurement signal representative of the number of said at least one type of law;

(i) computer means operatively connected to said analyzer means for receiving said measurement signal and for automatically calculating a control signal in response to said measurement signal, wherein said control signal has a first magnitude when said measurement signal is greater than a predefined number of said at least one type of flaw, and has a second magnitude when said measurement signal is less than said predefined number;

(j) means for manipulating said diverter valve in response to said control signal to thereby establish plastic pellet flow from said inlet of said diverter valve to said first outlet of said diverter valve when said control signal has said first magnitude, and to establish plastic pellet flow from said inlet of said diverter valve to said second outlet of said diverter valve when said control signal has said second magnitude;

(k) level detector means for establishing a first signal representative of the level of pellets in said holdup tank;

(l) means for establishing a second signal representative of a desired level of pellets in said hold up tank such that said second signal is a function of the feed rate to the hold up tank and the time involved in calculating said control signal in paragraph (i);

(m) a control valve operably located in said outlet of said hold up tank;

(n) a level controller means for comparing said first signal and said second signal and for establishing a third signal responsive to the difference between said first signal and said second signal, wherein said third signal is scaled so as to be representative of the position of said control valve required to maintain the actual level of the pellets in said hold up tank substantially equal to the desired level represented by said second signal; and (o) means for manipulating said control valve in response to said third signal so that the plastic pellets from which a side stream is withdrawn in (f) are delivered from said hold up tank to said diverter valve at substantially the same time that said diverter valve is being manipulated in response to the manipulating means in paragraph (j).

2. Apparatus in accordance with claim 1, wherein said analyzer includes laser means and means effective to produce a measurement signal that is representative of said at least one type of flow in a unit area of said film.

3. Apparatus in accordance with claim 1, wherein said analyzer includes laser means and means effective to produce a measurement signal that is representative of the number of gels in a unit area of said film that are larger than a predetermined size.

4. Apparatus in accordance with claim 1, wherein said analyzer includes laser means and means effective to produce a measurement signal which is representative of the number of black specks in a unit area of said film.

5. Apparatus in accordance with claim 1, wherein said analyzer means includes a laser beam and means for providing an output signal which is a function of laser light diffraction by said film.

6. Apparatus in accordance with claim 1 wherein said hold up tank is a vertically mounted tubular vessel having said inlet at the upper end, and said outlet at the lower end, wherein plug type flow is established through said hold up vessel.

* * * * *